United States Patent
Salonius et al.

(10) Patent No.: US 7,707,970 B2
(45) Date of Patent: May 4, 2010

(54) **VACCINE AGAINST SALMONID RICKETTSIAL SEPTICAEMIA BASED ON *ARTHROBACTER* CELLS**

(75) Inventors: Kira Salonius, Victoria (CA); Steven Gareth Griffiths, Moncton (CA)

(73) Assignee: Novartis AG, Basel (CH)

( * ) Notice: Subject to any disclaimer, the term of this patent is extended or adjusted under 35 U.S.C. 154(b) by 341 days.

(21) Appl. No.: 11/937,642

(22) Filed: Nov. 9, 2007

(65) Prior Publication Data

US 2009/0155313 A1    Jun. 18, 2009

Related U.S. Application Data

(62) Division of application No. 10/521,104, filed as application No. PCT/EP03/07605 on Jul. 14, 2003, now Pat. No. 7,302,913.

(30) Foreign Application Priority Data

Jul. 15, 2002  (GB) ................. 0216414.3
Aug. 29, 2002  (GB) ................. 0220100.2

(51) Int. Cl.
*A01K 61/00* (2006.01)
*A61K 39/00* (2006.01)
(52) U.S. Cl. .................... 119/215; 424/184.1
(58) Field of Classification Search ......... 119/215; 424/234.1, 184.1, 252.1, 243
See application file for complete search history.

(56) References Cited

U.S. PATENT DOCUMENTS

| | | | | |
|---|---|---|---|---|
| 6,627,203 B1 * | 9/2003 | Griffiths et al. | .......... | 424/234.1 |
| 6,913,754 B1 * | 7/2005 | Griffiths et al. | .......... | 424/234.1 |
| 2003/0165526 A1 * | 9/2003 | Kuzyk et al. | .......... | 424/190.1 |
| 2005/0202039 A1 * | 9/2005 | Griffiths et al. | .......... | 424/200.1 |
| 2006/0127416 A1 * | 6/2006 | Griffiths et al. | .......... | 424/234.1 |
| 2009/0162391 A1 * | 6/2009 | Kirke et al. | .......... | 424/190.1 |

* cited by examiner

*Primary Examiner*—Yvonne R. Abbott

(57) ABSTRACT

A vaccine based on live *Arthrobacter* cells is useful in preventing piscirickettsiosis in fish.

20 Claims, No Drawings

VACCINE AGAINST SALMONID RICKETTSIAL SEPTICAEMIA BASED ON *ARTHROBACTER* CELLS

CROSS REFERENCE TO RELATED APPLICATIONS

This application is a division of U.S. Ser. No. 10/521,104, filed on Feb. 14, 2005 now U.S. Pat. No. 7,302,913, the disclosure of which is fully incorporated herein by reference, which is a national phase application of International Application No. PCT/EP03/07605 filed on Jul. 14, 2003, claiming benefit of Great Britain Application No. 0216414.3, filed Jul. 15, 2002 and Great Britain Application No. 0220100.2 filed Aug. 29, 2002.

FIELD OF THE INVENTION

The present invention concerns use of a live strain of *Arthrobacter* in the preparation of a medicament to treat or prevent salmonid rickettsial septicaemia (SRS), and vaccines based on these bacteria.

BACKGROUND OF THE INVENTION

*Piscirickettsia salmonis* is a gram-negative obligate intracellular bacterium that causes systemic septicaemia (salmonid rickettsial syndrome, SRS, or piscirickettsiosis) in salmonid fish. *Piscirickettsia*—like bacteria are now been recognized with increasing frequency in a variety of other fish species, from both fresh and salt waters around the world. Piscirickettsiosis and piscirickettsiosis-like diseases have affected aquaculture productivity, profitability, the species compatible with commercial rearing, and transportation of fish from site to site. The Chilean aquaculture industry alone attributes annual losses to salmonid piscirickettsiosis of $150 million. In Chile, the syndrome has led to a shift from the more commercially desirable coho salmon to the less desirable but more piscirickettsiosis resistant Atlantic salmon as the primary cultivated species.

Antimicrobials have been tested as a therapy for SRS, but without consistent success. Other suggested measures include attempts to reduce stress in the fish by reducing stocking density, and removing dead fish from tanks without delay. The most practical solution to the SRS epidemic would be to find an effective vaccine to prevent the disease in the first place. Inactivated bacterin preparations from *P. salmonis* have been shown to have some protective effect, and may be the only suitable option for co-administration in multivalent oil preparations, but are relatively expensive to produce on a commercial scale. Vaccines based on recombinant antigens from *P. salmonis* have not yet reached the marketplace.

Accordingly, there is an urgent need to make available a vaccine capable of significantly reducing mortalities due to piscirickettsiosis in fish. The present invention is based on the surprising discovery that an existing commercial vaccine product is remarkably effective in preventing the disease. This vaccine is marketed under the name RENOGEN, a live, non-virulent strain of *Arthrobacter* vaccine. Currently, this vaccine is indicated to protect salmon and other farmed fish against bacterial kidney disease (BKD). The characteristics of this strain are disclosed in WO 98/33884, which is incorporated herein by reference.

SUMMARY OF THE INVENTION

In one aspect of the invention there is provided use of live *Arthrobacter* cells in the preparation of a medicament for the treatment or prevention of piscirickettsiosis in fish. The preferred targets of the medicament are salmonid fish exposed to risk of SRS infection. The *Arthrobacter* cells are preferably from the strain deposited under accession number ATCC 55921, or an equivalent strain.

In a second aspect of the invention there is provided a vaccine composition comprising live *Arthrobacter* cells and a killed bacterial immunostimulant, and a pharmaceutically acceptable carrier. In another aspect of the invention there is provided a vaccine composition comprising killed *Arthrobacter* cell material, and use of killed *Arthrobacter* cell material as an immunostimulant. The killed *Arthrobacter* cell material is preferably from the strain deposited under accession number ATCC 55921, or an equivalent strain.

In yet another aspect of the invention there is provided a vaccine composition comprising live *Arthrobacter* cells and inactivated *Piscirickettsia salmonis* antigen, whereby the vaccine is optionally provided in the form of a kit comprising a lyophilized *Arthrobacter* live cell culture and a sterile diluent comprising the inactivated *P. salmonis* antigen.

In a further aspect of the invention there is provided a method of treatment or prevention of piscirickettsiosis in fish comprising administering to fish in need of such treatment a vaccine comprising live *Arthrobacter* cells.

DETAILED DESCRIPTION OF THE INVENTION

RENOGEN vaccine has been in use for some time to combat Bacterial Kidney Disease (BKD) in salmonid fish. This vaccine is unique in that it is the first live culture to have been licensed for use in aquaculture, and comprises a live culture of *Arthrobacter* sp. nov., deposited under Accession No ATCC 55921 with the American Type Culture Collection (10801 University Boulevard, Manassas, Va. 20110-2209) on 20 Dec. 1996. *Arthrobacter* is not pathogenic to fish; nor is it the causative agent of BKD (which is *Renibacterium salmoninarum*).

It was observed on one site in the field that use of RENOGEN in a salmon population at risk of contracting BKD led to a dramatic reduction in mortality rates compared to untreated fish. Average weight gain in the RENOGEN-treated group was 18% greater than in the untreated fish group. SRS was also common on the site, which led the present inventors to speculate that RENOGEN may have conferred hidden protection against SRS as well as BKD.

In order to test this concept, tank-held fish were immunized with RENOGEN and subsequently challenged with *P. salmonis*, as described in Example 2. In the negative control group, which had received saline injections, nearly all the fish succumbed to SRS. The test groups that had received the RENOGEN vaccine exhibited extremely low mortality rates after 471 dd (degree days), amounting to between 88 and 100 relative percent survival (RPS). Even after 1441 dd (equivalent to one year in sea water) the test groups had a RPS of between 69 and 85%, compared to only 48.6% in the inactivated *P. salmonis* "gold standard" group.

Further evidence of the potential for vaccination with RENOGEN is demonstrated by the cross-reactivity of *P. salmonis* antigen when probed with rabbit polyclonal anti-*Arthrobacter* antibodies (Example 1).

We have shown that RENOGEN is more effective than any other known vaccine in preventing SRS. Live *Arthrobacter* bacteria are known to be able to enter cells and replicate for a limited period of time. The present inventors believe that this permits the antigen processing of both carbohydrate and protein antigens with sufficient homology to T-cell epitopes of *P. salmonis* to provide a high level of protection to direct challenge with virulent *P. salmonis*.

The invention therefore provides for the use of *Arthrobacter* cells in the preparation of a medicament for the treatment or prevention of piscirickettsiosis in fish, in particular salmonid fish, including salmon and trout species, particularly Coho salmon (*Oncorhyncus kisutch*), Chinook salmon (*Oncorhynchus tshawytscha*), masu salmon (*Oncorhyncus masou*), pink salmon (*Oncorhynchus gorbuscha*), rainbow trout (*Oncorhynchus mykiss*), and Atlantic salmon (*Salmo salar*). However, any other fish species susceptible to piscirickettsiosis or similar disease may benefit, such as, *Tilapia* sp., Black seabass (*Dicentrarchus* sp.), White seabass (*Atractoscion nobilis*), grouper fish, cichlids etc.

RENOGEN is based on a particular deposited strain of *Arthrobacter* (ATCC 55921). In performing the present invention, this strain or equivalent *Arthrobacter* strains can be employed. Equivalent *Arthrobacter* strains share the identifying characteristics of *Arthrobacter* ATCC 55921. They display similar protective capabilities against SRS. A species of *Arthrobacter* having an identical 16S rDNA sequence or a 165 rDNA sequence having a divergence of less than 3% with the strain ATCC 55921 is regarded as being equivalent. This 165 rDNA sequence is deposited under Genbank accession number AF099202. Another method of defining an equivalent strain is by RAPD assay using the F12-373 primer (5'-ACGGTACCAG-3' (SEQ ID NO:1)), as described in Griffiths, SG et al. (1998) Fish & Shellfish Immunology 8: 607-619. A distinctive fragment of about 373 bp is generated when this assay is performed on *Arthrobacter* ATCC 55921 and equivalent strains. An alternative RAPD assay described in the same publication using primers RsxII-67f (5'-CTGTGCTTGCACGGGGGATTA-3'(SEQ ID NO:2)) and RsxII-284r (5'-GTGGCCGGTCACCCTCTCAG-3'(SEQ ID NO:3)) yields a 260 bp fragment when performed on *Arthrobacter* ATCC 55921 or equivalent strains.

Species of the *Arthrobacter* genus are numerous and abundant in diverse habitats, including marine environments. Many *Arthrobacter* strains are available from commercial depositary institutions. It is not unduly burdensome on the skilled person to screen a selection of known strains or newly-isolated strains for the identifying characteristics and/or SRS immunogenic properties identified herein. SRS immunogenic properties can be identified by the screening assays described in the preceding paragraph and/or by the experimental procedures described in Example 1 and Example 2.

The preferred route of administration of the vaccine is by injection into the peritoneal cavity but other administration options exist, including orally in feed, by intra-dermal or intra-muscular injection, or by immersion in sea water or in fresh water. Fish are usually anaesthetized before receiving the vaccine by injection. It is recommended that fish be 10 grams or greater in body weight for administration of the vaccine of the invention by intraperitoneal injection. For immersion or oral administration, a body weight of at least 2 grams is preferred.

The effective dosage of vaccine may vary depending on the size and species of the subject, and according to the mode of administration. The optimal dosage can be determined through trial and error by a veterinarian or aquaculture specialist. A suitable dosage range may be from about $10^2$ to $10^9$ cfu per unit dose, preferably about $10^4$ to $10^7$ cfu per unit dose, more preferably about $10^5$ to $10^6$ cfu per unit dose, and most preferably about $10^5$ cfu per unit dose. However, higher or lower doses may also be effective. Preferably a single dosage unit is administered to the fish to be treated. Smaller fish may benefit from a dose of about $10^4$ to $10^7$ cfu/ml with dip (immersion) administration, for instance with a contact time of about 60 seconds. For immersion administration the vaccine may be diluted in 1 to 10 volumes of water before adding to tanks or cages holding fish.

A preferred dosage volume for injections is about 0.05-0.5 ml, preferably 0.075-0.25 ml, more preferably 0.1-0.2 ml, optionally about 0.1 ml.

Due to the dependence of development of immunity on the water temperature, it is preferred that fish are not exposed to SRS infection until at least 400 degree days after vaccination with the *Arthrobacter* vaccine of the invention (degree days=no. of days×average water temperature in ° C.).

In one embodiment of the invention, live *Arthrobacter* cells are combined with a pharmaceutically acceptable carrier or vehicle in a pharmaceutical composition. Suitable carriers/vehicles include conventional excipients, and may be, for example, solvents such as water, oil, or saline, dextrose, glycerol, wetting or emulsifying agents, bulking agents, coatings, binders, fillers, disintegrants, diluents, lubricants, pH buffering agents, or conventional adjuvants such as muramyl dipeptides, avridine, aluminium hydroxide, oils, (e.g. mineral oil), saponins, block co-polymers and other substances known in the art. A preferred pharmaceutical composition comprises a saline diluent.

Typically, vaccines are prepared as liquid solutions or suspensions for injection or for delivery in water. Solid (e.g. powder) forms suitable for dissolution in, or suspension in, liquid vehicles, or for mixing with solid food prior to administration may also be prepared. Preferably the vaccine is a lyophilised culture. In this form the vaccine is suitable for reconstitution with a sterile diluent. For instance, lyophilized cells may be reconstituted in 0.9% saline (optionally provided as part of the packaged vaccine product). The pharmaceutical vaccine compositions of the invention may be administered in a form for immediate release or extended release.

In one embodiment the *Arthrobacter* vaccine of the invention comprises an immunostimulant. The immunostimulant may be any known immunostimulant, but it is preferably a killed bacterial preparation. Preferably the immunostimulant is killed *Arthrobacter* cell material, which is optionally heat killed and is optionally from a culture of *Arthrobacter* ATCC 55921. Suitable examples of killed bacterial preparations include: PEPTIMUNE (a heat-killed *Arthrobacter* ATCC 55921 culture) and ULTRACORN (ultrasonicated *Corynebacterium cutis* lysate). An optimal dosage of killed bacterial immunostimulant is (per vaccine unit dose) 1 to 100 μg, preferably in the range 5 to 50 μg, more preferably 10 to 20 μg and optionally about 12 μg of cellular matter. The killed bacterial immunostimulant is optionally dissolved or suspended in sterile diluent (e.g. saline) for mixing with lyophilized live *Arthrobacter* cells.

The invention in one aspect provides a vaccine composition comprising live *Arthrobacter* cells and further comprising at least one other immunogen (where an "immunogen" is defined as a molecule such as an antigen capable of raising a specific immune response in a fish). The immunogen is optionally selected from the group consisting of: inactivated antigen prepared from *Piscirickettsia salmonis* (*P. salmonis*); a recombinant *P. salmonis* antigen; and a nucleic acid vector carrying an expressible *P. salmonis* antigen. In some instances it may be desirable to combine the RENOGEN vaccine of the invention with a conventional SRS vaccine (*P. salmonis* bacterin or recombinant antigen vaccine or nucleic acid vaccine) in a kit comprising both components for separate, sequential or simultaneous administration, for treatment or prevention of SRS.

In a preferred embodiment the invention relates to a vaccine comprising live *Arthrobacter* cells and inactivated *P. salmonis* antigen, and optionally killed *Arthrobacter* cell material as an immunostimulant. The *P. salmonis* antigen can be prepared by inactivation using any known inactivating agent, but is preferably prepared by formalin inactivation. *P. salmonis* antigen can be prepared from any isolate of the bacteria. Optionally, strain LF-89 deposited under ATCC number VR-1361, or a strain derived therefrom, is used to prepare the inactivated antigen.

A suitable procedure for inactivating the *P. salmonis* antigen is by harvesting the supernatant from *P. salmonis* infected CHSE-14 cell cultures and adding formalin (37% formaldehyde solution) to a final concentration of 0.125% (v/v). The culture fluid/formalin mixture is stirred to homogeneity and then held at 4±2° C. with constant agitation for a minimum of 72 hours. The inactivated harvest material may be concentrated by sterile ultra-filtration. A suitable final concentration of the *P. salmonis* antigen preparation defined by an enzyme immunoassay (EIA) ratio expressed as $OD_{405/490}$ of the antigen/$OD_{405/490}$ standard, is 1.5±0.2 units.

The combination of *Arthrobacter* and *P. salmonis* components in a single vaccine leads to a significant augmentation of protection against SRS compared to the live *Arthrobacter* cell vaccine alone. In an SRS challenge trial similar to that described in Example 2, it was shown that over the long term (past 1400 degree days) the bivalent vaccine adds greater than 20 RPS (relative percent survival) points compared with the monovalent live *Arthrobacter* vaccine.

Preferably this vaccine is produced and sold in the form of a kit comprising a lyophilized culture of live *Arthrobacter* cells, together with a sterile diluent such as saline in which the inactivated *P. salmonis* antigen (and optionally a killed bacterial immunostimulant) is dissolved or suspended. For instance, the *P. salmonis* antigen prepared made as described above can be mixed with the diluent at a concentration of between about 10 to about 150 ml/litre, preferably about 20 to about 100 ml/litre, and most preferably 75 ml/litre.

It is also within the scope of the invention to prepare multivalent vaccines comprising live *Arthrobacter* cells and antigens from pathogens other than *P. salmonis*.

All of the vaccines of the invention which incorporate *Arthrobacter* live cells not only protect against SRS but also give rise to protection of fish against BKD infection.

EXAMPLES

Example 1

Cross-Reactivity of *P. salmonis* Antigen with Anti-*Arthrobacter* Polyclonal Antibodies Approximately 25 μg of triple-washed *P. salmonis* bacterial cells harvested from CHSE-214 cell culture were mixed with 100 μl of Laemmli buffer and heated at 95° C. for 3 minutes. 10 μl samples were loaded onto a 9% acrylamide gel and electrophoresed at 150 volts for 1 hour to separate out the proteins. The proteins were transferred onto 100% nitrocellulose membrane using a semi-dry transblotter (BIORAD). The protein transfer was performed at 20 volts for 50 minutes.

The blot was incubated with 20 μl of rabbit anti-*Arthrobacter* polyclonal antibodies for 45 minutes in 15 ml of 1% casein tris-borate saline (cTBS). The blot was then exposed to 5 μl of goat anti-rabbit immunoglobulin alkaline phosphatase (GAR-AP), and developed. Several proteins were highlighted on the blot, indicating that anti-*Arthrobacter* protein antibodies have a strong affinity to certain *P. salmonis* proteins. This result was also confirmed on a 2D Western blot.

This experiment shows that certain *P. salmonis* and *Arthrobacter* proteins cross-react, indicating that these *Arthrobacter* proteins can prime the immune system to produce antibodies potentially capable of recognizing and protecting against *P. salmonis* virulent bacteria.

Example 2

Protectivity of an *Arthrobacter* Vaccine Against SRS

Coho salmon (n=110 per treatment group, mean weight 10 g) were maintained under normal husbandry conditions in tank water according to standard operating procedures at 12° C. Following one week of acclimatization Groups 1, 2 and 3 were vaccinated intraperitoneally with 0.1 ml of $10^5$, $10^6$, and $10^7$ cfu/dose, respectively, of lyophilized *Arthrobacter* sp. nov cells (RENOGEN) reconstituted in saline diluent. Groups 4 and 5 were treated in an identical manner to Group 1, but with the addition of 12.2 μg and 50 μg per dose, respectively, of PEPTIMUNE in the saline diluent. Groups 6 and 7 were positive controls vaccinated with *P. salmonis* bacterin. The bacterin was prepared from the supernatant of a *P. salmonis* type strain LF-89 infected CHSE-14 cell culture using 0.125% formalin at 4° C. over a minimum 72 h period. U/F concentration was employed and the concentrated supernatant was used to incorporate 8 μg (protein) per 0.1 ml dose. The bacterin vaccine was delivered with ULTRACORN (Virbac, France) at 20 (Group 6) and 100 μg (Group 7) per fish. The antigens were emulsified with an equal volume of mineral oil adjuvant prior to injection. The negative control group (Group 8) received an injection of saline.

TABLE 1 summarizes the treatment groups (dose volume (0.1 mL per fish) for 20 mls):

| Group | Treatment | Antigen Concentrate (ml) | Ultracorn (20 mg/ml) | Saline (ml) | Oil Adjuvant (ml) |
|---|---|---|---|---|---|
| 1 | $10^5$ cfu RENOGEN | nil | nil | 1 vial/1000 ml | |
| 2 | $10^6$ cfu RENOGEN | nil | nil | 1 vial/in one ml (99 ml saline) | |

TABLE 1-continued summarizes the treatment groups (dose volume (0.1 mL per fish) for 20 mls):

| Group | Treatment | Antigen Concentrate (ml) | Ultracorn (20 mg/ml) | Saline (ml) | Oil Adjuvant (ml) |
|---|---|---|---|---|---|
| 3 | $10^7$ cfu RENOGEN | nil | nil | 2 vials/2 ml (18 ml saline) | |
| 4 | $10^5$ + 100 ml (12.2 µg per dose PEPTIMUNE) | | | as 1 | |
| 5 | $10^5$ + 400 ml (50 µg per dose PEPTIMUNE) | | | as 1 | |
| 6 | *P. salmonis* bact. 20 µg -3x | 3 | 0.2 | 6.8 | 10 |
| 7 | *P. salmonis* bact. 100 µg -3x | 3 | 1.0 | 5.8 | 10 |
| 8 | Saline | | | 0.1 | |

Challenge Method

At 471 and 1441 dd (degree days) following vaccination, duplicate groups of 25 fish per treatment were challenged with virulent *P. salmonis* by intraperitoneal injection. Virulent *P. salmonis* was cultured on CHSE-14 cells for a minimum of 2-3 weeks. Supernatants of culture reaching at least 50% CPE were used for the i.p. injections. The virulent *P. salmonis* injections were given at $10^{-2}$ dilutions or more at 0.1 ml per fish (n=25). Challenged fish were maintained at 12° C.

Before termination of the challenge 1, 10 fish from the surviving populations of Group 1, 7 and 8 (only 8 fish were survivors in this group) were sacrificed and a splenic and renal tissue sample of 0.5 g was taken, homogenized and diluted in 10 ml of tissue culture medium. A $TCID_{50}$ was determined on 96 well plates containing confluent CHSE-214 cells.

Results and Discussion:

TABLE 2

Mortality during the 28 d safety test, maintained at 9-12° C. through-out the safety and pre-challenge period.

| Group | Treatment | Tank | Loss per treatment (N) | Total (N) | % Mortality |
|---|---|---|---|---|---|
| 1 | RENOGEN $10^5$ dose | I1 | 0 | 110 | 0 |
| 2 | RENOGEN $10^6$ dose | I2 | 0 | 110 | 0 |
| 3 | RENOGEN $10^7$ dose | I3 | 7 | 110 | 6.3 |
| 4 | RENOGEN $10^5$ dose + 12.2 µg PEPTIMUNE | I4 | 1 | 110 | 0.9 |
| 5 | RENOGEN $10^5$ dose + 50 µg PEPTIMUNE | I5 | 4 | 110 | 3.6 |
| 6 | *P. salmonis* 20 U/Oil | I6 | 0 | 110 | 0 |
| 7 | *P. salmonis* 100 U/Oil | I7 | 0 | 110 | 0 |
| 8 | Saline | I8 | 0 | 110 | 0 |

During the safety study, it was observed that fish in Group 3 suffered some loss (6.3%) nearing the end of the 28 d safety period. The lab investigator treated all fish in the population with a three day formalin treatment for bacterial gill disease. Mortality (3.6%) in Group 5 was recorded during the initial three day period pv, indicating that the inclusion of PEPTIMUNE as 40% of the diluent was somewhat toxic. No positive plates were cultured from the losses during the safety period, either for the live vaccine strain, or any incidental bacterial cultures.

TABLE 3

Cumulative Mortality and Relative Percent Survival of Coho salmon (mean weight 10 g) 471 dd post-vaccination with *Arthrobacter* sp. nov cells (Groups 1-5), Inactivated SRS vaccines, or saline when challenged with virulent *P. salmonis* by intraperitoneal injection ($TCID_{50}$ 3 × $10^{2.9}$ per fish) at 12° C.

| Group | Treatment | Tank | Loss per duplicate tank (N) | Total | Loss per treatment | % Mort | RPS |
|---|---|---|---|---|---|---|---|
| 1 | RENOGEN $10^5$ dose | L1, L2 | 0/25, 1/25 | 50 | 1/50 | 2 | 97.6 |
| 2 | RENOGEN $10^6$ dose | L3, L4 | 1/26, 0/24 | 50 | 1/50 | 2 | 97.6 |
| 3 | RENOGEN $10^7$ dose | L5, L6 | 2/25, 3/25 | 50 | 5/50 | 10 | 88.1 |

TABLE 3-continued

Cumulative Mortality and Relative Percent Survival of Coho salmon (mean weight 10 g) 471 dd post-vaccination with *Arthrobacter* sp. nov cells (Groups 1-5), Inactivated SRS vaccines, or saline when challenged with virulent *P. salmonis* by intraperitoneal injection (TCID $_{50}$ 3 × 102.9 per fish) at 12° C.

| Group | Treatment | Tank | Loss per duplicate tank (N) | Total | Loss per treatment | % Mort | RPS |
|---|---|---|---|---|---|---|---|
| 4 | RENOGEN $10^5$ dose + 12.2 µg PEPTIMUNE | L7, L8 | 0/25, 0/25 | 50 | 0/50 | 0 | 100 |
| 5 | RENOGEN $10^5$ dose + 50 µg PEPTIMUNE | L9, L10 | 0/25, 0/25 | 50 | 0/50 | 0 | 100 |
| 6 | *P. salmonis* 20 U/Oil | L11, L12 | 9/25, 12/25 | 50 | 21/50 | 42 | 50.0 |
| 7 | *P. salmonis* 100 U/Oil | L13, L14 | 7/25, 6/25 | 50 | 13/50 | 26 | 69.1 |
| 8 | Saline | L15, L16 | 19/25, 23/25 | 50 | 42/50 | 84 | — |

At 471 dd post-vaccination, fish in Group 1 had a relative percent survival (RPS) of 97.6, a high level of protection from direct infection with *P. salmonis* over 32 days, where mortality in the saline control group was 84%. This compared favourably to the protection garnered from vaccination with the standard inactivated vaccines (Groups 6 and 7), that showed RPS values of 50 and 69% respectively.

TCID$_{50}$ Analysis of Surviving Fish in Group 1, 7 and 8.

TABLE 4

Level of SRS infection in the tissue samples of the surviving fish from the 471 dd challenge (n = 7 – 10), 32 days post-infection:

| Group | Treatment | % of fish TCID$_{50}$ >$10^2$/mL | Mean TCID$_{50}$ |
|---|---|---|---|
| 1 | RENOGEN | 20 | 104.5/mL |
| 7 | *P. salmonis* 100 U/oil | 44 | 104.6/mL |
| 8 | Saline | 50 | 104.7/mL |

The TCID$_{50}$ of the fish sampled from the RENOGEN group was lower than the inactivated vaccine group, and both were lower than the saline controls. This is not of apparent clinical relevance, as the contribution of the high titre groups negates the lower infective dosages when averaging. However, the RENOGEN group did have the lowest percent positives (<20%) as samples with less than $10^2$ were considered not to be clinically infected with SRS. This compares to the same samples from the saline control group where 50% of the fish were positive for SRS, and favourably to the inactivated vaccine group with 44% of the fish positive for SRS.

TABLE 5

Cumulative Mortality and Relative Percent Survival of Coho salmon (mean weight 10 g) 1441 dd post-vaccination with *Arthrobacter* sp. nov cells (Groups 1-5), Inactivated SRS vaccines, or saline when challenged with virulent *P. salmonis* by intraperitoneal injection (TCID 3 × 102.9 per fish) at 12° C.

| Group | Treatment | Tank | Loss per duplicate tank (N) | Total | Loss per treatment | % Mort | RPS |
|---|---|---|---|---|---|---|---|
| 1 | RENOGEN $10^5$ dose | L1, L2 | 8/25, 3/25 | 50 | 11/50 | 22 | 69.4 |
| 2 | RENOGEN $10^6$ dose | L3, L4 | 2/24, 3/25 | 49 | 5/49 | 10.2 | 85.8 |
| 3 | RENOGEN $10^7$ dose | L5, L6 | 3/19, 2/19 | 38 | 5/38 | 13.2 | 81.7 |
| 4 | RENOGEN $10^5$ dose + 12.2 µg PEPTIMUNE | L7, L8 | 4/25, 5/25 | 52 | 9/52 | 17.2 | 76.1 |
| 5 | RENOGEN $10^5$ dose + 50 µg PEPTIMUNE | L9, L10 | 2/24, 5/24 | 48 | 7/48 | 14.6 | 79.7 |
| 7 | *P. salmonis* 100 U/Oil | L11, L12 | 10/23, 7/23 | 46 | 17/43 | 37 | 48.6 |
| 8 | Saline | L13, L14 | 20/25, 16/25 | 50 | 36/50 | 72 | — |

Note: back-up fish in Group 6 intended for the long term efficacy study were lost due to accidental shut-off of water flow in this tank (17).

After an elapsed period of 1140 dd, the durational response of the protection observed at the earlier test period (471 dd) was assessed. Results of the second challenge where a level of 72% mortality was observed in the saline control group indicate that the level of protection is still high with RENOGEN treated fish (69.4% RPS), with some indication that a higher dosage may improve the long term protection ($10^6$ and $10^7$ cfu/dose had RPS of 85.8 and 81.7 respectively). The addition of the immunostimulant PEPTIMUNE at 12 and 50 μg to the diluent provided an improvement to the efficacy of the product at dose (76.1 and 79.7% respectively). The accidental loss of the standard reference vaccine (group 6) allowed for comparison to Group 7 only, and this group had an RPS of 48.6%.

CONCLUSIONS

RENOGEN provided significant protection against direct challenge with *P. salmonis* at 471 dd and at 1441 dd post-vaccination. The vaccine was superior to the protection provided by the standard oil vaccine. We were able to demonstrate that fewer surviving fish in the RENOGEN group were clinically infected with *P. salmonis*. The study demonstrates that *Arthrobacter* sp. nov. live vaccine provides a high degree of protection against *P. salmonis* infection, and that the protective effect is shown to be long-term. Inclusion of a killed *Arthrobacter* preparation in the vaccine had an immune-stimulating effect resulting in improved survival rates.

We claim:

1. A method of treating or preventing a disease in a fish, the method comprising:
    administering to the fish an immunogenic composition comprising an *Arthrobacter*, wherein the disease is caused by *Piscirickettsia salmonis*.
2. The method of claim 1, wherein the disease is piscirickettsiosis.
3. The method of claim 1, wherein the fish is a salmonid fish.
4. The method of claim 1, wherein the fish is *Salmo salar*.
5. The method of claim 1, wherein the fish is an *Ocnorhyncus* species.
6. The method of claim 1, wherein the fish is selected from the group consisting of: *Oncorhyncus kisutch, Oncorhyncus tshawytscha, Oncorhyncus masou, Oncorhyncus gorbuscha,* and *Oncorhyncus mykiss*.
7. The method of claim 1, wherein the fish is an *Oncorhyncus kisutch*.
8. The method of claim 1, wherein the *Arthrobacter* is live.
9. The method of claim 8, wherein the composition further comprises a killed *Arthrobacter*.
10. The method of claim 1, wherein the *Arthrobacter* is killed.
11. The method of claim 1, wherein the *Arthrobacter* is an *Arthrobacter* species deposited under ATCC accession no. 55921.
12. The method of claim 1, wherein the *Arthrobacter* is a species having a 16S rDNA sequence that is identical to or

SEQUENCE LISTING

<160> NUMBER OF SEQ ID NOS: 3

<210> SEQ ID NO 1
<211> LENGTH: 10
<212> TYPE: DNA
<213> ORGANISM: Artificial Sequence
<220> FEATURE:
<223> OTHER INFORMATION: Primer

<400> SEQUENCE: 1
acggtaccag                                                          10

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
ctgtgcttgc acgggggatt a                                             21

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
gtggccggtc accctctcag                                               20 less than 3% divergent to the 16S rDNA sequence of an *Arthrobacter* species deposited under ATCC accession no. 55921.

13. The method of claim 1, wherein the composition further comprises at least one immunogen other than the *Arthrobacter*.

14. The method of claim 13, wherein the at least one immunogen is a *Piscirickettsia salmonis* antigen.

15. The method of claim 14, wherein the *Piscirickettsia salmonis* antigen is a nucleic acid expression vector capable of expressing the *Piscirickettsia salmonis* antigen.

16. The method of claim 13, wherein the at least one immunogen is a *Piscirickettsia salmonis*.

17. The method of claim 16, wherein the *Piscirickettsia salmonis* is inactivated.

18. The method of claim 16, wherein the *Piscirickettsia salmonis* is killed.

19. The method of claim 1, wherein the administering is by intraperitoneal injection of the fish.

20. The method of claim 1, wherein the administering is by immersion of the fish.

* * * * *